United States Patent [19]
Gulcicek et al.

[11] Patent Number: 5,432,343
[45] Date of Patent: Jul. 11, 1995

[54] ION FOCUSING LENSING SYSTEM FOR A MASS SPECTROMETER INTERFACED TO AN ATMOSPHERIC PRESSURE ION SOURCE

[76] Inventors: Erol E. Gulcicek, 360 Highland Ave., #2E, Cheshire, Conn. 06410; Craig M. Whitehouse, 220 Pleasant Point Rd., Branford, Conn. 06405

[21] Appl. No.: 71,441
[22] Filed: Jun. 3, 1993
[51] Int. Cl.6 .................. B01D 59/44; H01J 49/00
[52] U.S. Cl. ....................... 250/288; 250/282
[58] Field of Search ........... 250/281, 282, 288, 288 A, 250/423 R

[56] References Cited

U.S. PATENT DOCUMENTS

| | | | |
|---|---|---|---|
| 4,121,099 | 10/1978 | French et al. | 250/281 |
| 4,542,293 | 9/1985 | Fenn et al. | 250/288 |
| 5,122,670 | 6/1992 | Mylchreest et al. | 250/281 |
| 5,157,260 | 10/1992 | Mylchreest et al. | 250/423 R |

Primary Examiner—Bruce C. Anderson
Attorney, Agent, or Firm—Levisohn, Lerner, Berger & Langsam

[57] ABSTRACT

This invention describes an ion focusing lensing system and method interfaced between an atmospheric pressure ion source and a mass spectrometer in which the proper positioning of an electrostatic lens within a transition flow pressure region may be used to increase the transmission efficiency of ions to the mass spectrometer. The described configuration allows an increase in ion transmission efficiency to be gained in a manner independent from the operational voltages in the viscous flow pressure region, thereby allowing independent adjustment of the desired degree of collisionally induced dissociation and declustering processes. In addition, proper placement of the electrostatic lens in the transition flow region allows for collimation of the ion beam, enhancing ion beam transmission into the mass spectrometer aperture.

27 Claims, 4 Drawing Sheets

ION FOCUSING LENSING SYSTEM FOR A MASS SPECTROMETER INTERFACED TO AN ATMOSPHERIC PRESSURE ION SOURCE

BACKGROUND OF THE INVENTION

1. Field of the Invention

This invention relates to mass spectrometry and more specifically to atmospheric pressure ion sources such as Electrospray (ES) and Atmospheric Pressure Chemical Ionization (APCI). The invention includes means for increasing the efficiency of ion transmission from atmospheric pressure into the mass analyzer at high vacuum.

2. Background Art

The Electrospray ionization technique, and more specifically Electrospray ionization sources interfaced to mass spectrometers, have opened a new era of study for the molecular weight determination of labile and involatile biological compounds. The ES technique can produce singly or multiply charged ions in the gas phase from solution at atmospheric pressure. The mass to charge of the ions produced by ES depends on the analyte's molecular weight and solution chemistry conditions. The production of singly and multiply charged ions by electrospray ionization at atmospheric pressure is extensively described by Fenn et al. in U.S. Pat. No. 5,130,538.

Typically, only a small portion of the ions produced at atmospheric pressure can be effectively sampled and transported into high vacuum where they are mass analyzed using a mass spectrometer. For practical and cost reasons, limited pumping speeds are employed in mass spectrometer instrumentation. Consequently, only a limited amount of ion laden atmospheric pressure gas can be "leaked" into vacuum through a small orifice. The gas exiting from a sampling orifice, usually a nozzle or a capillary tube, undergoes a supersonic expansion as it expands into vacuum. As only a limited number of ions produced can be sampled through this orifice into vacuum, it is important to focus as many ions as possible through the region of expanding gas and on into the mass analyzer. The more efficiently the ions are decoupled from the expanding carrier gas and focused into the mass analyzer, the higher is the sensitivity of the overall instrument. Various numbers of pumping stages have been used to remove the gas entering a vacuum system through an orifice from atmospheric pressure and different apparatus and electrostatic lens geometries have been employed to improve the efficiency of ion transmission through specific pumping stage configurations.

Descriptions of ion sources which operate at atmospheric pressure such as ES and APCI interfaced to mass analyzer systems are found in U.S. Pat. Nos. 5,157,260; 5,015,845; 4,999,493; 4,977,320; 4,542,293; 4,531,056; 4,209,696; 4,144,451; 4,137,750; 4,121,099; 4,023,398. In all of these ES and APCI mass spectrometry assemblies, there is a nozzle or a capillary tube orifice communicating between the atmospheric pressure ionization region and the lower pressure viscous flow region at the beginning of the free jet expansion. Typically, a conical skimmer with a small circular aperture is located downstream of the nozzle or capillary exit. The skimmer orifice samples a portion of the gas expanding in the free jet, effectively serving to separate the higher pressure viscous gas flow of the free jet found in the first vacuum pumping stage from subsequent vacuum pumping stages which are maintained at lower background pressure. Most mass analyzers generally operate in vacuum pressures well within the free molecular flow regime. Once ions pass through the first skimmer orifice, they may be required to pass through one or more additional pumping stages before entering the mass analyzer. Background pressures in the first pumping stage or viscous flow regime can be as high as a few torr and the background pressures usually required by mass analyzers with electron multiplier detectors fall below $1 \times 10^{-5}$ torr. One exception to this mass analyzer vacuum requirement is the ion trap or three dimensional quadrupole mass spectrometer. Pressures used inside ion trap mass spectrometers can run much higher than other types of mass analyzers; however, the ion detectors still require pressures in the $10^{-5}$ torr range or better. Hence, even for ion trap mass spectrometers there is a need for efficient ion transmission from the higher viscous flow vacuum pressure region into the non-viscous flow region of the trap analyzer and ion detector.

In U.S. Pat. No. 5,157,260 a tube shaped focusing lens is described, situated inside the first pumping stage of the free jet expansion formed from gas expanding through a capillary tube from atmospheric pressure into vacuum. Gas flow between the capillary exit and the skimmer orifice as described in this patent is in the viscous flow regime, so the mean free path of molecules in this portion of the free jet molecules is quite small. The patent claims that as a result of the voltages applied to the tube lens, the ion densities near the centerline of the free jet which pass through the first skimmer orifice are enriched. U.S. Pat. No. 4,121,099 shows a conical shaped lens 70, (FIG. 7) located in the free jet expansion region between the nozzle and the first skimmer in the first pumping stage of a mass spectrometer. Voltage applied to this conical lens in the viscous flow regime of the first pumping stage of the expanding free jet helps to concentrate the ions entrained in the carrier gas closer to the center line. This enriches the ion density near the center line so that more ions can be effectively sampled through the first skimmer. It was also found that application of certain voltages to the lens elements of this viscous flow free jet region can effectively cause breaking of non-covalently bound complexes such as clusters and even covalent bonds of the ions entrained in the free jet.

Applying focusing and accelerating voltages to focusing lenses in the viscous flow region accelerates the ions along electrostatic field lines between collisions with the neutral expanding carrier gas. The net result is that the ions can be driven to follow different trajectories than the neutral carrier gas but because the mean free path between collisions is so short in this viscous flow region, the ion velocities achieved are only the local mobility limit for the local electrostatic field and gas pressure for a given ion. This mobility velocity is so slow that little translational energy in terms of electrostatic energy is imparted to the ion in the first pumping stage viscous flow regime. The repeated collisions of ions with the neutral carrier gas can, however, increase the ion's internal energy resulting in collisionally induced dissociation (CID) of that sampled ion. This effect in many cases is desirable to the user where one can reproducibly generate fragment ions by adjusting the voltage difference between the focusing and the adjacent lenses without suffering the wide range of energy spreads associated with non-viscous pressure regime CID processes used in mass spectrometric analysis. The CID technique in the free jet expansion region of an electrospray ion source is widely used and can yield important structural and identification information of molecules that are being analyzed (See, for example, Smith et. al, J. Am. Soc. Mass Spectrom., Vol. 1, p. 53, 1990). As mentioned above, the collisions in this area can also be used to decluster the solvent molecules from the analyte ions of interest which had not been effectively removed before the ion entered the free jet expansion.

The present invention describes an electrostatic lens located in the transition or slip flow pressure regime downstream of the first skimmer. This electrostatic lens aids in concentrating and focusing ions along the centerline, effectively increasing the ion transmission efficiency into the mass analyzer. This lens configuration with the appropriate applied voltages causes ion enrichment and centerline focusing of the ion beam even in a pressure region where a significant number of collisions with the neutral carrier gas are still occurring. In addition, the lensing system allows for increased ion transmission independent of the operational voltages of the lenses in the viscous flow pressure region where the degree of CID and declustering processes can be adjusted separately. The free flight relative electrostatic energy of the ion being focused in vacuum is not established until the gas pressure of neutral background gas is decreased to the molecular flow region. In the molecular flow vacuum region ions can be accelerated by electrostatic forces with negligible loss of translational energy from collisions with background gas. The present invention addresses a lens configuration which focuses ions in the transition or slip flow pressure region after the viscous flow region and before or as they enter the free molecular flow region. Voltage settings can then be applied to maximize ion transmission and collimate the ion beam through this vacuum regime where collisions with background neutral gas still occur. The invention described is particularly useful for multiple pumping stage systems with progressively lower pressure per vacuum stage. The ion beam is focused and the ion energy is set just after the transition pressure region between viscous flow and free molecular flow vacuum regions resulting in an overall increase in ion transmission efficiency from an atmospheric pressure ion source into a mass analyzer. The use of multiple pumping stages can increase overall system sensitivity at lower cost. Removing more gas on a mass basis at higher pressures allows greater throughput for less cost than trying to remove the same gas mass loading at lower pressures with larger vacuum pumps. For example, it is more cost effective to remove gas with rotary pumps than with diffusion, turbomolecular, or cryopumps. Multiple staged pumping systems allow the removal of much gas with rotary pumps in the first and even the second vacuum stage effectively reducing the gas load on the lower pressure vacuum stages. Critical to the performance of such staged vacuum pumping systems is the efficiency in ion transmission from the viscous to free molecular flow region where the ions can be electrostatically focused and accelerated with little effect from collisions with neutral background gas.

SUMMARY OF THE INVENTION

It is an object of this invention to provide an increased ion transmission efficiency for ions created at atmospheric pressure and transported to a mass analyzer in vacuum so that greater sensitivity and overall performance can be achieved for analysis of sample compounds.

It is a further object of this invention to provide the increased ion transmission into the mass analyzer while allowing optimum conditions to be adjusted independently in the viscous pressure region of jet expansion where collisionally induced dissociation and declustering processes can occur.

It is a further object of this invention to adjust the relative potential of the ions prior to entering the free molecular flow regime, to provide a collimated beam of ions entering the mass analyzer to minimize the number of ion optic focusing lenses in the free molecular flow pressure region and to minimize the lens electrostatic potential variation when optimizing for the transmission of ions of different molecular weight.

The aforementioned and other objects of this invention are realized by using an additional differential pumping stage whose pressure falls in the transition flow regime separating the viscous flow and the free molecular flow regions, and by installing an electrostatic lens in this transitional pressure region positioned between the orifices through which ions enter and exit the pumping stage. By applying the appropriate electrostatic voltages to the lens between the orifice through which ions enter from the viscous pressure regime and the orifice leading to the third pumping stage the electrostatic fields are shaped such that the ions are pulled closer to the centerline and focused while some collisions with background gas are occurring.

BRIEF DESCRIPTION OF THE DRAWINGS

The objectives and features of this invention will be better understood if followed in conjunction with the accompanying drawings in which.

DETAILED DESCRIPTION OF THE INVENTION

The Electrospray ionization source which will be specifically described is one possible example of an atmospheric pressure ion source, although the lens system described can be applied to an APCI ion or other atmospheric pressure ion sources as well. Once ions are produced at atmospheric pressure and transported into vacuum through a nozzle or capillary tube, the ion to background or carrier gas ratio must be amplified in the vacuum pumping and ion transport regions to achieve efficient ion transmission into deeper vacuum and on into the mass analyzer. To achieve this, as the background gas is pumped away, the ions being transmitted are accelerated and focused with electrostatic lenses into the entrance of a mass analyzer. In the viscous and transition vacuum pressure regions, the electrostatic lenses must be shaped and positioned to most efficiently focus ions to the centerline while the ions are experiencing a significant number of collisions with the background gas. Preferably the lenses located in the vacuum pumping stages should be configured to minimize interference with flow of background gas away from the centerline as it is pumped away in each progressive vacuum stage.

Figure 1:
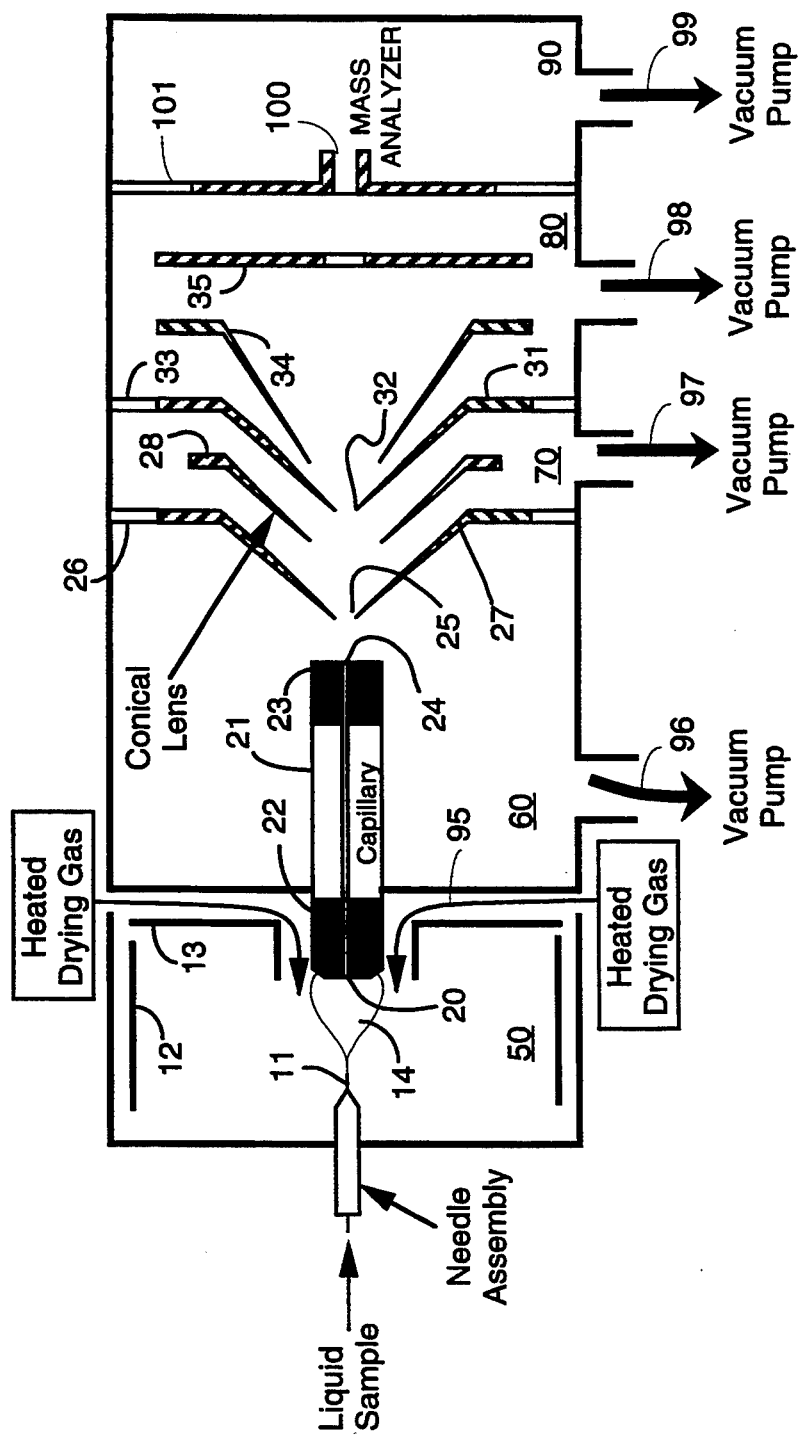
FIG. 1 shows the schematic representation of an atmospheric pressure Electrospray ion source interfaced to a mass analyzer with one embodiment of the invention included.

FIG. 1 provides a schematic representation of an atmospheric pressure ion source interfaced to a mass spectrometer configuration. The Electrospray ionization source chamber 50 is at atmospheric pressure and includes a sharp tipped electrically conducting tubing 11 through which sample bearing liquid is introduced. Sufficient voltage is applied between this tube tip 11 and the electrically conductive end 22 of a capillary tube 21, the end-plate lens element 13 and the cylindrical lens element 12, until a spray of charged liquid droplets 14, is formed from the sample bearing liquid emerging from tube 11. The additional lenses 12 and 13 are used to help enrich the concentration of charged droplets near the centerline where the ions which desorb from the charged droplets can be more efficiently swept into the capillary entrance orifice 20. Heated counter-current drying gas as illustrated by the arrows 95 in FIG. 1 flows into the Electrospray chamber 50 counter-current to the charged droplet movement 14. This counter-current drying gas effectively causes the charged liquid droplets to evaporate leading to the desorption of sample ions from the liquid droplets into the gas phase. A portion of these desorbed ions are swept into the capillary orifice 20 by the flowing drying or carrier gas and transported through capillary 21 by the gas flowing through the capillary tube exiting at orifice 24 into vacuum. The background pressure in the first vacuum pumping stage 60 is usually maintained below 10 torr and typically is on the order of 1 to 5 torr so that the gas exiting capillary 21 through the exit orifice 24 forms a supersonic free jet expanding into the first vacuum pumping stage 60. Ions entrained in the neutral gas flowing through the capillary are swept along into the free jet by the neutral gas expanding into vacuum. The capillary exit 23 and skimmer element 27 are electrostatically conductive and voltages are applied to these elements to enrich the concentration of ions near the centerline. Ions near the centerline are carried through the first skimmer orifice 25 into the second pumping stage 70.

The vacuum system configuration diagrammatically illustrated in FIG. 1 includes four vacuum pumping stages. This configuration is one preferred embodiment, however, the invention could be applied to a system with more or less pumping stages. In the configuration illustrated, the first pumping stage 60 is evacuated through pumping port 96. The second pumping stage 70 is evacuated through pumping port 97. The third pumping stage 80 is evacuated through pumping port 98 and the fourth pumping stage 90 is evacuated through pumping port 99. The first skimmer 27 is electrically isolated on mounting plate 26 and separates the first 60 and second 70 pumping stages. The second skimmer 31 is electrically isolated on mounting plate 33 and separates the second 70 and third 80 pumping stages. The mass analyzer entrance aperture 100 is electrically isolated on plate 101 which separates the third 80 and fourth 90 pumping stages. The distance between the capillary exit 24 and the first skimmer aperture 25 is such that viscous flow is present across all or most of this region. The background pressure in the second pumping stage 70 is maintained generally between 2 and 400 millitorr. Pressure along the centerline in vacuum stage two will vary from a high at skimmer one aperture 25 to a low at skimmer two aperture 32. Background pressure in the third pumping stage 80 is maintained in or below the $10^{-4}$ torr region with background pressure in the fourth pumping stage usually maintained below $1 \times 10^{-5}$ torr. In the preferred embodiment illustrated in FIG. 1, an electrostatic focusing lens 28 is mounted in pumping stage two between the first 27 and second 31 skimmer elements. Additional electrostatic lenses 34 and 35 are positioned in pumping stage three. Ions exiting the capillary exit orifice 24 must traverse three pumping stages before entering the mass analyzer through aperture 100. Increasing the efficiency of transporting these ions into the mass analyzer increases the overall instrument sensitivity for mass analysis of compounds.

Figure 2:
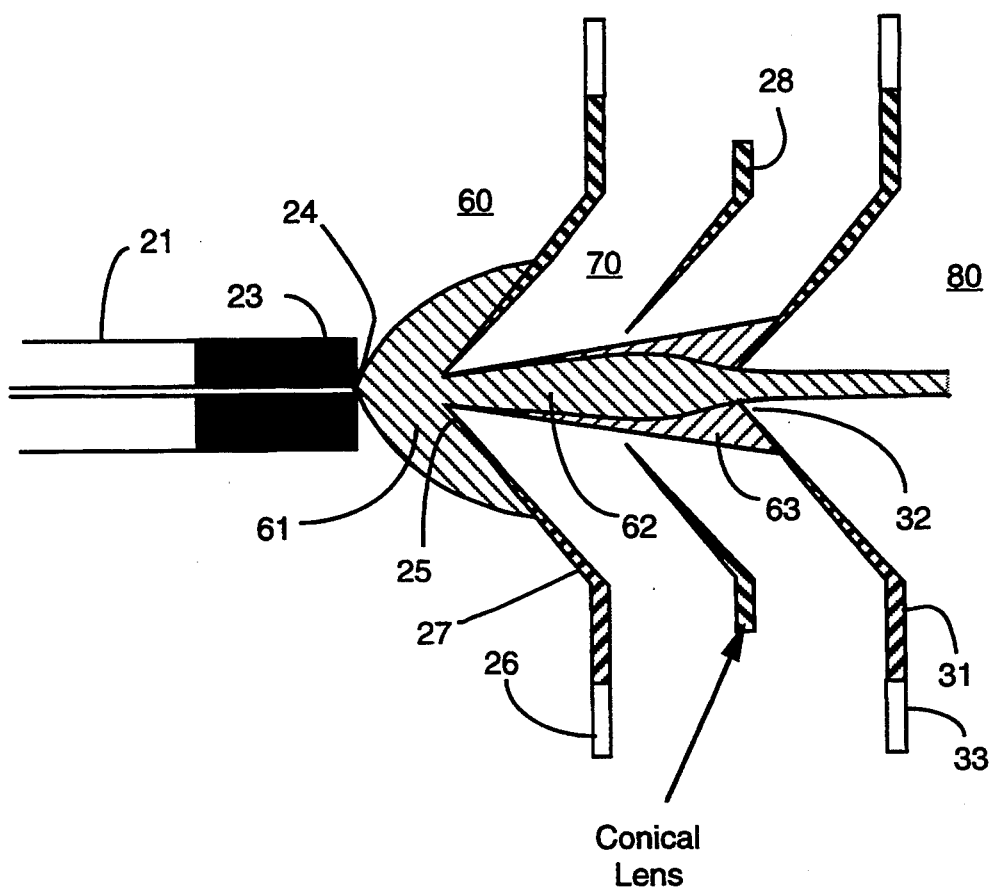
FIG. 2 shows a schematic view of the electrostatic lenses and skimmers in the first two pumping stages of the electrospray ionization mass spectrometer interface including a preferred embodiment of this invention.

As described above, both the ions and the drying gas from the ionization region are expanded into the first vacuum pumping stage 60 from the exit aperture 2,4 of the capillary 21 through a supersonic free jet expansion 61 (FIG. 2). In order to optimize the ion transmission into the next pressure region 70 through the aperture 25, a voltage difference is applied between the conductive end 23 of capillary 21 and the first skimmer 27. This voltage difference can be further adjusted to yield fragment ions and, typically, the larger the voltage difference between the two, the higher is the fragment ion yield. Ions are pulled through the viscous pressure region of the expanding gas by the electrostatic field between the capillary end 23 and skimmer 27. The mean free path in this region 61 is so short, the ions are only accelerated from collision to collision such that not much increase in translation velocity is attained due to the electrostatic forces applied. As the ions and neutral gas enter the second pumping stage 70 through skimmer aperture 25 the neutral gas continues to expand as shown by the shaded area 63. Significant numbers of collisions between the ions and background gas continue as the ions progress into the second pumping stage 70. As gas is pumped away, the mean free path increases as the distance from skimmer aperture 25 increases. In this transition pressure region electrostatic lens 28 has been added to specifically shape the electrostatic field in the second pumping stage 70 to increase ion transmission as indicated by the shaded area 62 through skimmer orifice 32 and on into the mass analyzer through aperture 100.

In the transition pressure region, the ion collisions with background gas still interfere with purely electrostatic acceleration. To achieve the most efficient ion transmission and focusing along the centerline, the gas dynamics must be taken into account when optimizing the electrostatic fields. Mounting a lens between skimmers 27 and 31 allows for the needed application of electrostatic fields with minimal disruption in the neutral gas expansion. The optimal relative placement of lens 28 along the centerline has some dependence on the operating background pressure in the second pumping stage 70. When lens 28 placement is optimized for a given background pressure, the voltage applied to lens 28 to maximize ion transmission along the centerline is usually set relative to the potential set on skimmer 27. The ion transmission efficiency increases a factor of four to six with the addition of electrostatic lens 28 in or near the transition pressure region of pumping stage two. The location along the centerline in the second pumping stage where the ions enter the free molecular flow region is roughly defined as that location where ion traversing the region no longer experiences significant numbers of collisions with the background gas. It is the position where the electrostatic forces dominate the ion trajectories and velocity. The relative electrostatic field at the position the ion clears away from background collisions and can free fly is the point at which the ion energy relative to the mass analyzer entrance potential is established. The specific location of the beginning of free molecular flow along the centerline largely depends on the background pressure in the second pumping stage. The lower the background pressure the closer this point moves toward skimmer 17. The approximate location of the beginning of free molecular flow can be determined by measuring the ion energy using stopping potentials and comparing the measured energy with the known field based on electrostatic potentials set on skimmers 27 and 31 and lens 28. This information can be used to locate the position of lens 28 along the centerline for optimal performance. An example of determining the location of the beginning of free molecular flow for a specific background pressure in the second pumping stage is given in FIGS. 3 and 4.

Figure 3:
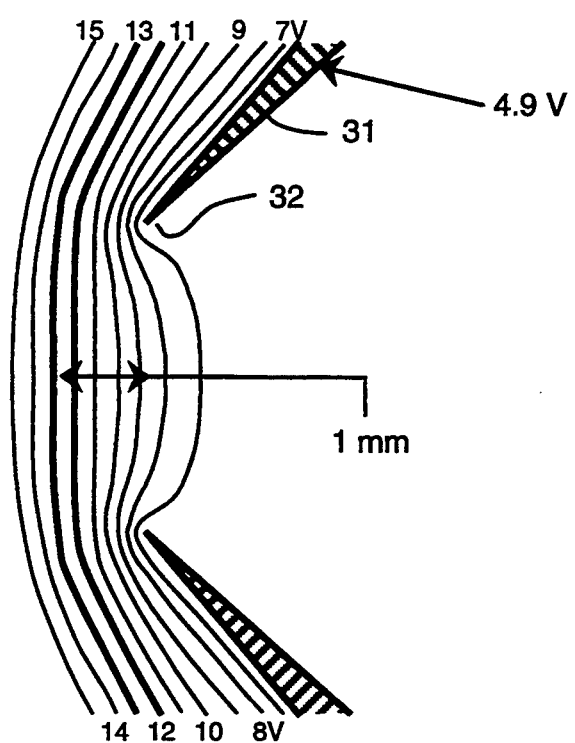
FIG. 3 shows a diagrammatic view of one example of the electrostatic field lines near the aperture of the skimmer which separates vacuum pumping stages two and three.
Figure 4:
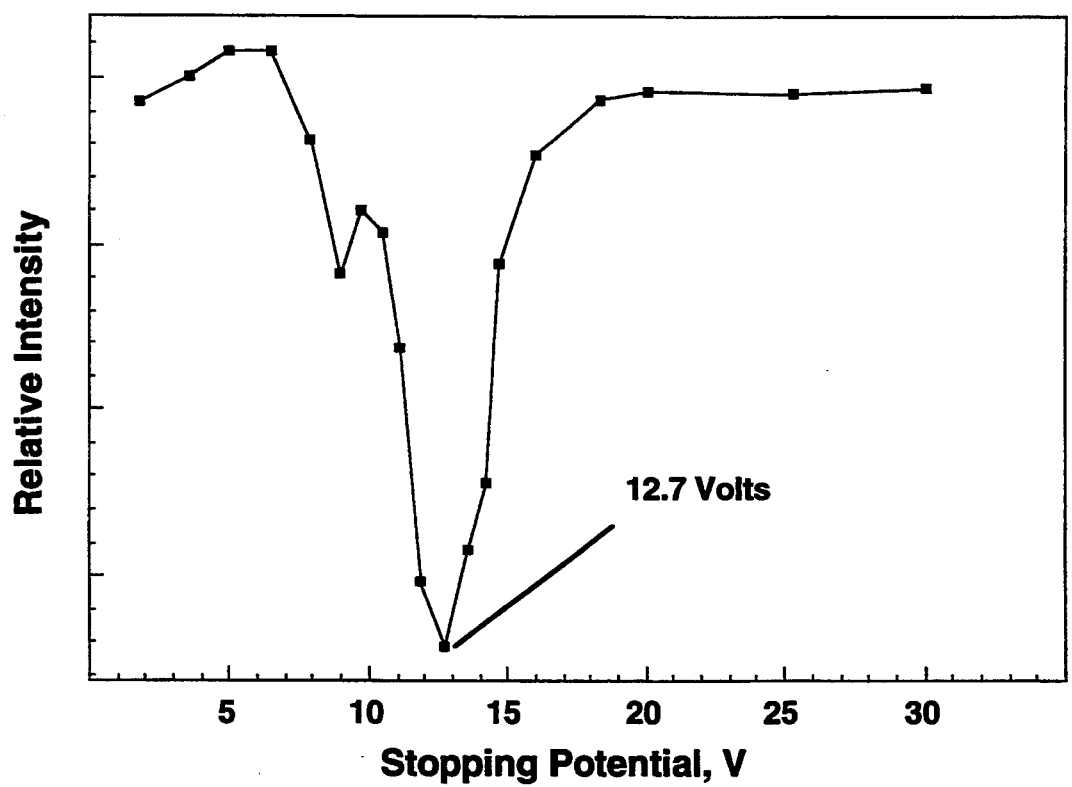
FIG. 4 shows an example of the stopping potential distribution of ions transmitted through vacuum pumping stage two for one particular background pressure in that pumping stage.

FIG. 3 is a map of the electrostatic field near the aperture 32 of skimmer 31 where the skimmer 31 potential was set at 4.9 volts relative to the zero volt mass analyzer entrance aperture 100 potential. For an optimal voltage setting on lens 28 of 32.1 volts, the stopping potential of a doubly charged ion with a mass to charge ratio of 571 is illustrated in the measured ion signal curve given in FIG. 4. The average measured stopping potential of approximately 12.7 Volts mapped back to an electrostatic field position of 12.7 volts falling roughly 1 mm upstream of the plane of the skimmer 31 aperture 32. This mapping of measured stopping potential directly onto a field potential map must include a correction factor for the translational energy added to the ion due to gas collisional acceleration in the free jet expansion but is a means to quickly determine the extent of the transition pressure region and to aid in optimal placement of lens 28.

Further ion beam studies have shown that relatively collinear ion trajectories were obtained into the analyzer region as a result of the addition and proper positioning of lens 28 in the transition flow pressure region 70. The collinear features of ion beams are particularly important for reducing any discrimination in ion transmission efficiency as a function of ion mass or molecular weight to charge. Ions entering the transition pressure region may have different energies imposed from the free jet expansion. By creating a collinear ion beam with lens 28 focal points are eliminated in the ion beam. Ions with different energies would have different focal points for a given lens potential setting. Eliminating a focal point in an ion beam reduces transmission discrimination into aperture 100 allowing a single relative lens potential setting to be optimal over a wide range of ion mass to charge values. Typical ion beam diameters at the location of aperture 100 were measured to be 2 to 3 mm with very small divergence angles thus allowing efficient transfer into the mass analyzer.

The above invention has been described with a preferred embodiment. Other variations of this invention may be generated by those of ordinary skill in the art which do not depart from the protection afforded by the claims herein.

What is claimed is:

1. An ion source apparatus for mass spectrometric analysis comprising an ionization region maintained at about atmospheric pressure for ionizing a sample, said ionization source interfaced to a vacuum pressure region of at least two stages, the first of which comprises a viscous flow pressure region and is maintained at viscous flow pressures at about 1 to 10 torr and the second of which comprises a transition flow pressure region and is maintained at transition flow pressures at about 5 to 300 millitorr, said ion source apparatus interfaced to a mass analyzer through said vacuum pressure region which is maintained at highly evacuated free molecular flow pressures at its upstream side, an orifice communicating between the said ionization region and the said viscous flow region, an electrically conductive first skimmer partition having an aperture separating said viscous flow pressure region from said transition flow pressure region, and a second electrically conductive skimmer partition having an aperture separating the said transition flow pressure region from said free molecular flow pressure region, wherein said transition flow pressure region includes an area which is the approximate beginning of free molecular flow, the improvement comprising a conductive lens located in the said transition flow pressure region between the said first and second skimmer partitions and means for concentrating the ions towards the axis of ion propagation.

2. An ion source apparatus according to claim 1, further comprising means for applying voltages to said conductive lens and to said first and second skimmer partitions.

3. An ion source apparatus according to claim 2, wherein said voltages are of different values.

4. An ion source apparatus according to claim 1 wherein said conductive lens comprises a conical lens having an aperture so dimensioned as to not interfere with the ion beam.

5. An ion source apparatus according to claim 1, wherein said conductive lens is positioned so as to provide minimal disruption to the neutral gas expansion.

6. An ion source apparatus according to claim 1, further comprising electrospray ionization means located in said ionization region.

7. An ion source apparatus according to claim 1, further comprising atmospheric pressure chemical ionization means located in said ionization region.

8. An ion source apparatus according to claim 1, wherein the voltage difference adjusted between the said conductive lens and the second skimmer partition provides kinetic energy to the ions at approximately said area of free molecular flow within the transition flow pressure region.

9. An ion source apparatus according to claim 1, wherein the conductive lens is located in the transition flow pressure region to collimate the ion trajectories in said ion beam to reduce the number of focal points in said ion beam.

10. An ion source apparatus according to claim 1, wherein said conductive lens is movable in said transition flow pressure region.

11. An ion source apparatus according to claim 1, wherein said conductive lens is located within the vicinity of the area of free molecular flow within said transition flow pressure region.

12. An ion source apparatus according to claim 1, further comprising electrostatic lenses within the free molecular flow pressure region.

13. An ion source apparatus according to claim 1, wherein said orifice comprises a dielectric capillary tube having an axial bore.

14. In an ion source apparatus for mass spectrometric analysis comprising an ionization region maintained at about atmospheric pressure for ionizing a sample, said ionization source interfaced to a vacuum pressure region of at least two stages, the first of which comprises a viscous flow pressure region and is maintained at viscous flow pressures at about 1 to 10 torr and the second of which comprises a transition flow pressure region and is maintained at transition flow pressures at about 5 to 300 millitorr, said ion source apparatus interfaced to a mass analyzer which is maintained at highly evacuated free molecular flow pressures at its upstream side, an orifice communicating between the said ionization region and the said viscous flow region, an electrically conductive first skimmer partition having an aperture separating said viscous flow pressure region from said transition flow pressure region, and a second electrically conductive skimmer partition having an aperture separating the said transition flow pressure region from said free molecular flow pressure region, an improved method of enhancing the sensitivity of the mass spectrometric analysis means comprising locating a conductive lens in the said transition flow pressure region between the said first and second skimmer partitions and concentrating the ions towards the axis of ion propagation.

15. The method of claim 14, further comprising the step of applying voltages to said conductive lens and to said first and second skimmer partitions.

16. The method of claim 15, wherein said voltages are of different values.

17. The method of claim 14, further comprising the step of reducing the number of focal points in said ion beam.

18. The method of claim 14, further comprising the step of collimating the ion trajectories in said ion beam to reduce the number of focal points in said ion beam.

19. The method of claim 14, comprising the further step of adjusting the degree of collisionally induced dissociation and declustering processes in said viscous flow pressure region.

20. The method of claim 14, further comprising the step of applying voltages to said dielectric capillary tube and to said first skimmer partition, comprising the further step of increasing said sensitivity independently of said voltages applied to said dielectric capillary tube and to said first skimmer partition.

21. The method of claim 14, comprising the further step of optimizing the location of said conductive lens to maximize the sensitivity of the mass spectrometric analysis.

22. The method of claim 14, comprising the further step of optimizing the location of said conductive lens to maximize the kinetic energy of the ions in the ion beam.

23. The method of claim 14, comprising the further step of increasing the kinetic energy of the ions in the ion beam at or near the area which is the approximate beginning of free molecular flow in the transition pressure region.

24. The method of claim 14, further comprising the step of determining the location of the area which is the approximate beginning of free molecular flow of said ions in said ion beam in said transition flow pressure region.

25. An ion source apparatus according to claim 14, comprising the further step of increasing the kinetic energy of the ions in the ion beam in the free molecular flow pressure region.

26. An ion source apparatus according to claim 14, comprising the further step of concentrating the ions in the ion beam toward the axis of ion propagation in the free molecular flow pressure region.

27. The method of claim 14, wherein said orifice comprises a dielectric capillary tube having an axial bore.

* * * * *